United States Patent [19]

Scott et al.

[11] 3,953,488

[45] Apr. 27, 1976

[54] METHOD FOR PREPARING ALIPHATIC AND CYCLOALIPHATIC ISOTHIOCYANATES

[75] Inventors: Peter H. Scott, Sudbury, Mass.; Ehrenfried H. Kober, Aschau near Kraiburg, Germany

[73] Assignee: Olin Corporation, New Haven, Conn.

[22] Filed: Aug. 2, 1971

[21] Appl. No.: 168,439

[52] U.S. Cl. ............................................... 260/454
[51] Int. Cl.² ..................................... C07C 161/04
[58] Field of Search ................................... 260/454

[56] References Cited
UNITED STATES PATENTS

| | | | |
|---|---|---|---|
| 3,427,355 | 2/1969 | Le Maistre et al. | 260/580 |
| 3,530,161 | 9/1970 | Hull | 260/454 |
| 3,535,362 | 10/1970 | Ottmann et al. | 260/454 |
| 3,637,820 | 1/1972 | Dodman et al. | 260/580 |
| 3,689,520 | 9/1972 | Smith | 260/454 |

FOREIGN PATENTS OR APPLICATIONS

| | | | |
|---|---|---|---|
| 1,159,638 | 7/1969 | United Kingdom | 260/586 |

*Primary Examiner*—Glennon H. Hollrah
*Attorney, Agent, or Firm*—Kenneth P. Glynn; Eugene Zagarella, Jr.

[57] ABSTRACT

A method for preparing aliphatic and cycloaliphatic isothiocyanates comprising reacting a selected aliphatic or cycloaliphatic nitro compound with a sulfur containing carbon compound in the presence of a metal carbonyl catalyst.

10 Claims, No Drawings

METHOD FOR PREPARING ALIPHATIC AND CYCLOALIPHATIC ISOTHIOCYANATES

This invention relates to the direct conversion of selected aliphatic and cycloaliphatic nitro compounds to the corresponding isothiocyanate. More particularly, this invention relates to the reaction of selected aliphatic and cycloaliphatic nitro compounds with a sulfur containing carbon compound in the presence of a metal carbonyl catalyst to obtain the respective isothiocyanate compound. The term "aliphatic" nitro compound as used throughout the specification and claims is intended to include both aliphatic and cycloaliphatic compounds.

Esters of isothiocyanic acid have been previously prepared. They are useful agricultural chemicals since they have exhibited valuable utility as fungicides and herbicides. Many of these esters are useful nematocides and insecticides particularly as moth-proofing agents. Isothiocyanates have also been extensively employed as intermediates in the preparation of pesticidal and pharmaceutical compounds. For instance, they have been reacted with stoichiometric amounts of chlorine to provide N-aryl- and N-alkyl-S-chloroisothiocarbamoyl chlorides, for example, as disclosed in *Journal of Organic Chemistry*, 31, 838 (1966); and these derivatives are useful as herbicides and nematocides. Isothiocyanates also react with a molar excess of chlorine to provide the corresponding isocyanide dichlorides which are known to be useful pesticides.

A variety of synthetic methods have been previously utilized to obtain the aforementioned esters. For example, they may be generally prepared by the reaction of primary amines with thiophosgene, but this is not a practical procedure since thiophosgene, is not readily available. Some of the isothiocyanates have been prepared by the reaction of isocyanate esters with phosphorus pentasulfide, but this is not a general reaction and cannot be utilized in the preparation of all isothiocyanates. The esters have also been prepared by an involved synthetic route comprising reacting primary amines with carbon disulfide in the presence of selected bases to provide salts of dithiocarbamic acids which can then be further reacted to the desired isothiocyanates, but this is a complicated and costly procedure.

It has now been found that selected aliphatic isothiocyanates can be prepared in a convenient, direct, one-step, economical method by reacting a selected aliphatic nitro compound with carbonyl sulfide and/or carbon disulfide in the presence of a metal carbonyl catalyst at ambient or an elevated temperature. This method is advantageous in that it avoids the previously disclosed tedious multi-step procedures and also utilizes readily available and inexpensive reactants.

In carrying out the method of this invention any aliphatic nitro compound capable of being converted into an aliphatic isothiocyanate may be employed as a reactant. More particularly the aliphatic nitro compounds which may be used in the method of this invention generally will contain from 1 to 22 carbon atoms and preferably from 1 to 14 carbon atoms. The aliphatic nitro compound may contain more than one nitro group, may be saturated or unsaturated and additionally may include other substituents such as nitroalkyl, alkyl, aryl, alkenyl, aralkyl, alkoxy, aryloxy, alkylthio, arylthio, carboxyalkyl, halogen, cyano, isocyanato, etc.

In general, these additional substituents do not inhibit completely the reaction of carbonyl sulfide or carbon disulfide with nitro groups under the conditions of the method disclosed therein. Carbon disulfide or carbonyl sulfide may also react with some of these additional substituents concurrently with the reaction of the nitro groups, and some of these substituents may impede or retard the desired reaction of carbonyl sulfide or carbon disulfide with the nitro groups as, for instance, by introducing a steric hindrance factor; but invariably some formation of aliphatic isothiocyanate occurs by the process albeit at a reduced rate.

Among the preferred aliphatic nitro compounds which may be utilized in the method disclosed herein are the nitroalkanes including, for instance, nitromethane, nitroethane, nitropropane, nitrobutane, nitrohexane, nitrooctane, nitrooctadecane, dinitroethane, dinitropropane, dinitrobutane, dinitrohexane, dinitrodecane, phenyl nitromethane, bromophenyl nitromethane, nitrophenyl nitromethane, methoxyphenyl nitromethane and the nitrocycloalkanes including for example, nitrocyclobutane, nitrocyclopentane, nitrocyclohexane, dinitrocyclohexane and bis(nitrocyclohexyl) methane. The terms aliphatic nitro compounds, nitroalkanes and nitrocycloalkanes as used throughout the specification and claims is intended to include both substituted and unsubstituted compounds.

Further examples or aliphatic nitro compounds which may be used include: 2,2-dimethyl-1-nitrobutane, 1-nitro-n-hexane, 1,4-dinitro-n-hexane, 1,6-dinitro-n-hexane, 1-fluoro-2-nitrocyclobutane, 1-chloro-2-nitrocyclobutane, 1-iodo-3-nitrocyclobutane, 1-methyl-2-nitrocyclobutane, 1-ethyl-3-nitrocyclobutane, 1-hexyl-3-nitrocyclobutane, 1-cyano-2-nitrocyclobutane, 1-methoxy-2-nitrocyclobutane, 1-bromo-3-nitrocyclopentane, 1-fluoro-2-nitrocyclopentane, 1-butoxy-3-nitrocyclopentane, 1-carboxyethyl-3-nitrocyclopentane, 1-ethylthio-3-nitrocyclopentane, 1-chloro-2-iodo-3-nitrocyclopentane, 1-methoxy-2-nitrocyclohexane, 1-ethoxy-4-nitrocyclohexane, 1-butenyl-2-nitrocyclohexane, 1-phenoxy-3-nitrocyclohexane, 1-iodo-3-nitrocyclohexane, 1-chloro-4-nitrocyclohexane, 1-cyano-2-nitrocyclohexane, 1-cyano-3-chloro-4-nitrocyclohexane, 1-ethoxy-4-iodo-5-nitrocyclohexane, 1-ethylthio-3-nitrocyclohexane, 1-carboxybutyl-3-nitrocyclohexane, 1-phenylthio-4-nitrocyclohexane, 1-carboxymethyl-3-nitrocyclohexane, 1-methyl-3-nitrocyclohexane, 1-phenoxy-4-nitrocyclooctane, 1-carboxymethyl-2-chloro-4-nitrocyclooctane, 1-ethyl-4-nitrocyclodecane, 1-cyano-5-nitrocyclodecane, 1-propenyl-6-nitrocyclodecane, 1-phenoxy-7-nitrocyclodecane, 1-carboxybutyl-6-nitrocyclodecane, 1-fluoro-3-chloro-4-nitrocyclododecane, 1-chloro-3-nitrocyclododecane, 1-carboxymethyl-4-nitrocyclododecane, 1-methylthio-4-nitrocyclododecane, 1-butenyl-4-nitrocyclododecane, 1-cyano-2-nitrocyclododecane, 1-phenoxy-2-nitrocyclododecane, 1-methylthio-5-nitrocyclotetradecane, 1-propenyl-4-nitrocyclotetradecane, 1-phenoxy-7-nitrocyclotetradecane, 1-butentyl-4-nitrocyclotetradecane, 1-butylthio-6-nitrocyclotetradecane, 1-propyl-5-nitrocyclotetradecane.

The above-noted aliphatic nitro compounds are merely exemplary and are not intended as an exclusive listing of the many compounds of this type which may be utilized. It is further noted that isomers and mixtures of the above-noted aliphatic nitro compounds as well as homologues and other related compounds may also be utilized.

Carbonyl sulfide (COS), carbon disulfide ($CS_2$) and mixtures thereof may be used as a second reactant in carrying out the method of this invention. For convenience, the term "sulfur-containing carbon compound" will be used throughout the specification and claims to include either carbon disulfide, carbonyl sulfide or mixtures thereof in any ratio.

The metal carbonyl catalyst employed in the method of this invention generally will be a carbonyl of iron, cobalt, nickel, or of an element of Group V-B or VI-B of the Periodic Table. Vanadium, niobium, tantalum, chromium, molybdenum and tungsten are the elements included in Groups V-B and VI-B of the Periodic Table. Examples of suitable carbonyl compounds include:

A. the simple metal carbonyls, such as:
   $V(CO)_6$
   $Cr(CO)_6$
   $Mo(CO)_6$
   $W(CO)_6$
   $Fe(CO)_5$
   $Ni(CO)_4$ B. polynuclear metal carbonyls, such as:
   $Fe_2(CO)_9$
   $Co_2(CO)_8$ C. metal carbonyl halides, such as:
   $Fe(CO)_5Br_2$
   $Fe(CO)_5Cl_2$
   $Fe(CO)_5I_2$
   $Fe(CO)_4Cl_2$
   $Fe(CO)_4I_2$
   $[Fe(CO)_3Br_2]_3$
   $[Fe(CO)_3Cl_2]_3$
   $Fe(CO)_2I_2$
   $Fe(CO)_2Br_2$
   $Fe(CO)_2I$
   $Fe(CO)_2Br$
   $Co(CO)I_2$
   $Fe(CO)_4ICl$
   $Fe(CO)_4IBr$ D. metal carbonyl hydrides, such as:
   $H_2Fe(CO)_4$
   $HCo(CO)_4$
   $H_2Fe_3(CO)_{11}$ E. metal carbonyl nitrosyls, such as:
   $Fe(CO)_2(NO)_2$
   $Co(CO)(NO)_2$
   $Fe(CO)_2NO$ F. inorganic and organic complexes and derivatives of the metal carbonyl compounds previously mentioned, such as:
   $V(CO)_6.PF_3$
   $Cr(CO)_6.NH_3$
   $Fe(CO)_5.PF_3$
   $Fe(CO)_5Br_2.NH_3$
   $V(CO)_6.(C_6H_5)_3P$
   $C_6H_6Cr(CO)_3$
   $C_5H_5V(CO)_4$
   $C_5H_5Co(CO)_2$
   $(C_5H_5Mo(CO)_3)_2$ and G. salts of metal carbonyls, such as:
   $Na[Co(CN)(CO)_3]$
   $Na[Ni(CN)(CO)_3]$
   $Na[Ni(CN)_2(CO)_2]$
   $K[Ni(CN)(CO)_3]$
   $K[Ni(CN)(CO)_3]$
   $Li[Ni(CN)(CO)_3]$
   $Li[Co(CN)(CO)_3]$
   $Na(C_6H_{14}O_3)_2V(CO)_6$ All of the carbonyl catalysts of the metals enumerated above are useful in the process of this invention, however, it has been found that the carbonyls of molybdenum, vanadium, chromium and iron are especially effective and preferred.

The metal carbonyl compounds employed as catalysts in the process of this invention which includes both liquids and solids, can be used in the pure state. The solid materials can be utilized in any convenient form in sufficient subdivision to provide an adequate surface, such as in granular, powdered, pelleted or crushed form. Also, it has been found that under certain reaction conditions improved reaction rates are obtained when the solid metal carbonyls are extended upon inert supports.

A satisfactory procedure for preparing a supported catalyst that can be used in practicing this invention involves deposition of a normally solid metal carbonyl from an organic solvent solution onto the supporting material. For example, a solution of the metal carbonyl in an aromatic hydrocarbon can be sprayed onto the desired carrier or the carrier can be immersed in a quantity of the hydrocarbon solution of the metal carbonyl in a suitable vessel. The deposited catalyst can then be dried at a temperature of about 80° to about 120°C. or higher to drive off the aromatic solvent and form a layer of the desired carbonyl compound on the support. Any of the well-known catalyst supports can be utilized including gamma alumina, any of the various silica-aluminas, activated clays, bauxite, silica, carbon, barium sulfate, calcium carbonate, asbestos, bentonite, fullers earth, etc. The supported catalyst can be used in the form of powder or pellets depending upon the type of reaction to be utilized. The use of pellets of approximately ⅛ inch size has proven to be surprisingly satisfactory in continuous flowing stream procedures, since this catalyst does not tend to wash out of the system in the flowing stream.

In carrying out the method of this invention, the amount of sulfur-containing carbon compound used is not particularly critical with the amount present being at least sufficient to provide reactant for the process. Generally the total amount of sulfur-containing carbon compound added during reaction is between about 1 and about 100 and preferably between about 2 and about 15 moles of sulfur-containing carbon compound per mole of nitro group in the aliphatic nitro compound. Greater or lesser amounts may be employed if desired but optimum yields of the aliphatic isothiocyanates are obtained when excess molar amounts are employed, that is, more than an equimolar quantity in reaction with a mononitro compound, for instance.

The reaction is conducted in the presence of a catalytic amount of the metal carbonyl catalyst. Usually between about 0.0001 to about 1 mole of catalyst are employed per mole of nitro group in the aliphatic nitro compound and preferably between about 0.02 to about 0.2 mole of the catalyst are utilized on the same basis. However, greater or lesser proportions of the catalyst may be utilized, if desired.

A solvent may be employed in the method of this invention if desired but is not required.

In conducting the method of this invention the temperature employed can be varied widely. Generally it will range from about 20° to about 250°C. and preferably will be from about 90° to about 165°C. Although the reaction can be conveniently carried out at atmospheric pressure, if desired, pressure ranges up to about 5000 psig. or more can be employed. Usually the reaction pressure will be from about atmospheric pressure to about 500 psig.

The reaction time will vary over a wide range depending upon the process conditions employed as well as the particular aliphatic nitro compound being reacted. Usually between about one-quarter to about 48 hours and preferably between about 1 to about 12 hours are required to obtain a satisfactory degree of reaction, however, shorter or longer reaction times may be employed.

A wide variety of apparatus can be employed in conducting the process described herein. For example, with atmospheric pressure reactions, the usual conventional closed kettles may be employed while at superatmospheric pressures, rocking-type as well as stirred autoclaves and tubular reactors may be employed. Preferably, some form of agitation, such as stirring, is supplied even when operating at atmospheric pressure. The process can be carried out batchwise, semicontinuously or continuously, as desired.

The following examples further illustrate the method of this invention.

EXAMPLE I

Nitrocyclohexane (0.02 mole), molybdenum hexacarbonyl (0.02 mole) and carbon disulfide (10 ml.) were heated in a 100 ml. rocking autoclave at 150°C. for three hours. The autoclave was cooled to room temperature, then opened and discharged of the reaction mixture. Unreacted $CS_2$ was evaporated from the reaction mixture by heating on a steam bath. The residue (1.61 g.), which showed a weak, broad infrared absorption at about 2050 $cm^{-1}$, was shown by vapor phase chromatographic (VPC) analysis to contain 57.4% nitrocyclohexane and 10.2% of a compound which was subsequently isolated as a VPC trap and shown by mass spectral analysis to be cyclohexyl isothiocyanate. The yield of cyclohexyl isothiocyanate was 8.9% based on unrecovered nitrocyclohexane.

EXAMPLE II

Nitrocyclohexane (0.02 mole) and molybdenum hexacarbonyl (0.0002 mole) were placed in a 100 ml. rocking autoclave which was then sealed. Carbonyl sulfide (10.0 g., 0.16 mole) was charged to the autoclave from a small stainless steel cylinder, in which it was contained in the liquified state under its own vapor pressure (about 160 psig). The autoclave was then heated at 150°C. for 3 hours, after which it was cooled to ambient temperature, vented and opened. The reaction mixture was rinsed from the autoclave with 10 ml. of chloroform. The chloroform solution was separated from an insoluble residue by filtration, following which the solvent was evaporated to give 0.97 g. of product mixture. Vapor phase chromatographic analysis of this mixture showed it to contain 1.0% of nitrocyclohexane and 3.6% of cyclohexyl isothiocyanate (1.3% yield based on unrecovered nitrocyclohexane).

What is claimed is:

1. A method for preparing aliphatic isothiocyanates comprising reacting:
   a. a nitroalkane or nitrocycloalkane containing from 1 to 22 carbon atoms with
   b. a sulfur-containing carbon compound selected from the group consisting of:
      1. carbonyl sulfide,
      2. carbon disulfide, and
      3. mixtures of carbonyl sulfide and carbon disulfide
   in the presence of
   c. a carbonyl of a metal selected from the group consisting of iron, nickel, cobalt, vanadium, niobium, tantalum, chromium, molybdenum and tungsten, said reaction being carried out at a temperature of from about 20° to about 250°C. and employing from about 1 to about 100 moles of said sulfur containing carbon compound per mole of nitro group in said nitroalkane or nitrocycloalkane and from about 0.0001 to about 1 mole of said carbonyl of a metal per mole of nitro group in said nitroalkane or said nitrocycloalkane.

2. The method of claim 1 wherein said nitroalkane or nitrocycloalkane contains from 1 to 14 carbon atoms.

3. The method of claim 2 wherein said carbonyl of metal is selected from the group consisting of molybdenum, vanadium, chromium and iron.

4. The method of claim 3 wherein said nitroalkane or nitrocycloalkane is nitrocyclohexane.

5. The method of claim 4 wherein said carbonyl of metal is molybdenum hexacarbonyl.

6. The method of claim 5 wherein said sulfur-containing carbon compound is carbon disulfide.

7. The method of claim 5 wherein said sulfur-containing carbon compound is carbonyl sulfide.

8. The method of claim 2 wherein said reaction is carried out at a pressure of from about atmospheric pressure to about 5,000 psig.

9. The method of claim 8 wherein the amount of sulfur containing carbon compound employed is from about 2 to about 15 moles per mole of nitro group in said nitroalkane or said nitrocycloalkane and the amount of said carbonyl of a metal employed is from about 0.02 to about 0.2 mole per mole of nitro group in said nitroalkane or said nitrocycloalkane.

10. The method of claim 9 wherein said reaction is run at a temperature of from about 90° to about 165°C.

* * * * *

UNITED STATES PATENT OFFICE
CERTIFICATE OF CORRECTION

Patent No. 3,953,488    Dated April 27, 1976

Inventor(s) Peter H. Scott and Ehrenfried H. Kober

It is certified that error appears in the above-identified patent and that said Letters Patent are hereby corrected as shown below:

Column 5, line 27, "(0.02 mole)" should read --(0.002 mole)--.

Column 5, line 44 "(0.0002 mole)" should read --(0.002 mole)--.

Signed and Sealed this

Third Day of August 1976

[SEAL]

Attest:

RUTH C. MASON
Attesting Officer

C. MARSHALL DANN
Commissioner of Patents and Trademarks